United States Patent [19]

Scripps

[11] Patent Number: 5,019,065
[45] Date of Patent: May 28, 1991

[54] DISPOSABLE ABSORBENT ARTICLE WITH COMBINATION MECHANICAL AND ADHESIVE TAPE FASTENER SYSTEM

[75] Inventor: Charles L. Scripps, Brookfield, Wis.

[73] Assignee: The Procter & Gamble Company, Cincinnati, Ohio

[21] Appl. No.: 479,232

[22] Filed: Feb. 12, 1990

Related U.S. Application Data

[63] Continuation of Ser. No. 134,278, Dec. 17, 1987, abandoned.

[51] Int. Cl.$^5$ ............................................. A61F 13/15
[52] U.S. Cl. ................................. 604/385.1; 604/389; 604/391
[58] Field of Search ............... 128/DIG. 15, DIG. 26; 604/389, 390, 386, 391, 387, 385.1–388.2

[56] References Cited

U.S. PATENT DOCUMENTS

| | | |
|---|---|---|
| 2,511,406 | 6/1950 | Israel . |
| 2,649,858 | 1/1951 | LeBolt . |
| 3,081,772 | 3/1963 | Brooks et al. . |
| 3,110,312 | 11/1963 | Wirth . |
| 3,138,841 | 6/1964 | Naimer . |
| 3,141,461 | 7/1964 | Farris . |
| 3,147,528 | 9/1964 | Erb . |
| 3,150,664 | 9/1964 | Noel . |
| 3,196,511 | 7/1965 | Kintner . |
| 3,359,980 | 12/1967 | Rosenblatt . |
| 3,559,648 | 2/1971 | Mason, Jr. . |
| 3,618,608 | 11/1971 | Brink . |
| 3,620,217 | 11/1971 | Gellert ............................. 604/390 |
| 3,653,381 | 4/1972 | Warnken . |
| 3,848,594 | 11/1974 | Buell . |
| 3,869,765 | 3/1975 | Schaar .............................. 604/390 |
| 3,882,871 | 5/1975 | Taniguchi . |
| 3,900,652 | 8/1975 | Uraya et al. . |
| 3,920,018 | 11/1975 | Schaar . |
| 3,931,666 | 1/1976 | Karami . |
| 3,955,575 | 5/1976 | Okuda . |
| 3,980,824 | 4/1976 | Karami ............................. 604/384 |
| 3,989,048 | 11/1976 | Cepuritis et al. .................... 604/390 |
| 4,005,712 | 2/1977 | Karami ............................. 604/390 |
| 4,014,340 | 3/1977 | Cheslow . |
| 4,051,854 | 10/1977 | Aaron . |
| 4,074,397 | 2/1978 | Rosin ........................... 128/DIG. 26 |
| 4,114,621 | 9/1978 | Mims, Jr. . |
| 4,127,132 | 11/1978 | Karami ............................. 604/390 |
| 4,158,906 | 6/1979 | Watson . |
| 4,169,303 | 10/1979 | Lemelson . |
| 4,241,462 | 12/1980 | Tagawa et al. . |
| 4,259,957 | 4/1981 | Sonnenstein et al. . |
| 4,290,174 | 9/1981 | Kalleberg . |
| 4,322,875 | 4/1982 | Brown et al. . |
| 4,380,450 | 4/1983 | Reich . |
| 4,402,690 | 9/1983 | Redfern . |

(List continued on next page.)

FOREIGN PATENT DOCUMENTS

0235014 9/1987 European Pat. Off. .

*Primary Examiner*—Randall L. Green
*Assistant Examiner*—K. Reichie
*Attorney, Agent, or Firm*—Steven W. Miller; John M. Pollaro; Richard C. Witte

[57] ABSTRACT

A disposable absorbent article with a combination mechanical and adhesive tape fastener system. The tape fastener system preferably comprises a tape tab comprising a first fastening element joined to and disposed on a first area of the tape tab and adhesive associated with and disposed on at least a second area of the tape tab. The adhesive not only secures the tape tab to the body portion of the absorbent article to provide a side closure but also secures the absorbent article in its disposal configuration so as to prevent the contents of the soiled absorbent article from spilling or leaking out of the absorbent article. Preferably, a portion of the adhesive is disposed subjacent the first fastening element to join the first fastening element to the tape tab.

31 Claims, 2 Drawing Sheets

U.S. PATENT DOCUMENTS

| | | |
|---|---|---|
| 4,410,327 | 10/1983 | Baggaley . |
| 4,475,912 | 10/1984 | Coates . |
| 4,509,512 | 4/1985 | LeClercq . |
| 4,537,591 | 8/1985 | Coates . |
| 4,541,154 | 9/1985 | Ito et al. . |
| 4,560,381 | 12/1985 | Southwell . |
| 4,568,342 | 2/1986 | Davis . |
| 4,576,599 | 3/1986 | Lipner . |
| 4,576,601 | 3/1986 | Brain . |
| 4,577,591 | 3/1986 | Wesseldine . |
| 4,581,772 | 4/1986 | Smith . |
| 4,585,450 | 4/1986 | Rosch et al. . |
| 4,610,680 | 9/1986 | LaFleur . |
| 4,617,022 | 10/1986 | Pignuel et al. . |
| 4,671,793 | 6/1987 | Hults et al. . |
| 4,680,030 | 7/1987 | Coates . |
| 4,681,581 | 7/1987 | Coates . |
| 4,699,622 | 10/1987 | Toussant et al. . |
| 4,728,326 | 3/1988 | Gilles . |
| 4,753,650 | 6/1988 | Williams . |
| 4,773,966 | 9/1988 | Krushel .................... 604/391 |
| 4,834,742 | 5/1989 | Wilson ...................... 604/391 |
| 4,846,815 | 7/1989 | Scripps . |
| 4,869,724 | 9/1989 | Scripps ..................... 604/389 |
| 4,894,060 | 1/1990 | Nestegard . |

DISPOSABLE ABSORBENT ARTICLE WITH COMBINATION MECHANICAL AND ADHESIVE TAPE FASTENER SYSTEM

This is a continuation of application Ser. No. 07/134,278, filed on Dec. 17, 1987, now abandoned.

FIELD OF THE INVENTION

This invention relates to fastening systems for disposable absorbent articles, and more particularly, to an improved tape fastener system for such disposable absorbent articles that provides a combination mechanical and adhesive tape fastener system.

BACKGROUND OF THE INVENTION

The use of adhesive tape fastener systems for securing the corners of a disposable absorbent article such as a diaper is well known in the art. Examples of these types of adhesive tape fastener systems are described in U.S. Pat. No. Re. 26,151 entitled "Disposable Diaper" which issued to Robert C. Duncan et al. on Jan. 31, 1967; and U.S. Pat. No. 3,848,594 entitled "Tape Fastening Systems for Disposable Diaper" issued to Kenneth B. Buell on Nov. 19, 1974.

Adhesive tape fastener systems provide a secure means for keeping a disposable absorbent article on the wearer during use. In addition, refastenable adhesive tape fastener systems allow the disposable absorbent article to be folded or rolled up into a tight package for disposal, secured in the disposal configuration, and easily disposed in waste receptacles. When such adhesive tape fasteners are secured to the rolled-up absorbent article, the contents of the absorbent article are generally prevented from spilling or leaking out while the absorbent article is being thrown away.

Adhesive tape fastener systems have, however, a number of shortcomings, one of which is that they are easily contaminated by oils and powders that come in contact with the adhesive positioned on the tape tabs such that the adhesive does not readily adhere to the absorbent article with sufficient strength to provide an effective side closure. In addition, an adhesive tape fastener system may cause the backsheet of the absorbent article to rip or tear when the fastener system is unfastened to check if the absorbent article has been soiled or to adjust its fit, thereby leaving a hole in the backsheet that renders the fastener system unrefastenable and the absorbent article unuseable. Thus, it would be advantageous to provide a fastener system that is not easily contaminated by oils and powders, that is more convenient to refasten, and that does not render the absorbent article or the fastener system unuseable after unfastening it.

A number of concepts have been proposed for providing washable diapers with mechanical fastening systems disposed on the body portion of the absorbent article. In addition, concepts of providing a disposable absorbent article with a tape fastener system having a mechanical fastening element have been proposed in U.S. patent application Ser. No. 078,345 entitled "Disposable Diaper Having Wide Tapered Fastening Tapes" filed by Harold R. Burkhard and Kenneth B. Buell on July 28, 1987, and my co-pending U.S. patent application Ser. No. 007,841 entitled "Disposable Diaper Having An Improved Fastening Device" filed on Jan. 26, 1987. While mechanical fastening systems, such as hook and loop-type mechanical fasteners, generally provide fastening systems that are not easily contaminated by oils and powders and that are more convenient for refastening than adhesive tape fastener systems, mechanical fastening systems are generally more expensive than adhesive tape fastener systems and do not provide a disposal mechanism by which the absorbent article may be rolled-up to contain the contents of the absorbent article and secured in that disposal configuration so that the absorbent article may be conveniently thrown away. Thus, it would be advantageous to provide a combination mechanical and adhesive tape fastener system.

It is, therefore, an object of the present invention to provide a disposable absorbent article having an improved fastening system.

It is a further object of the present invention to provide a disposable absorbent article having a combination mechanical and adhesive tape fastener system.

These and other objects of the present invention will be more readily apparent when considered in reference to the following description and when taken in connection with the accompanying drawings.

SUMMARY OF THE INVENTION

According to the present invention, a disposable absorbent article such as a diaper is provided with a combination mechanical and adhesive tape fastener system.

While the tape fastener system may take many configurations, it preferably comprises a tape tab comprising a first fastening element joined to and disposed on a first area of the tape tab and an adhesive securement means associated with and disposed on at least a second area of the tape tab; and a landing member comprising a second fastening element engageable with the first fastening element of the tape tab. In use, the first fastening element engages the second fastening element and the adhesive securement means is secured to either the second fastening element or a portion of the body portion of the absorbent article such as the backsheet to provide a secure side closure for the absorbent article. After the absorbent article has been soiled, it can be folded or rolled up into a configuration for disposal that generally prevents the contents of the soiled absorbent article from spilling or leaking out of the absorbent article. The absorbent article is then secured in its disposal configuration by the adhesive securement means.

The first fastening element and the adhesive securement means may be disposed on the tape in a number of configurations so long as a second area of adhesive securement means is exposed to provide a combination mechanical and adhesive closure mechanism. Preferably, the first fastening element and the adhesive securement means are each entirely disposed on the user's end of the tape tab with the first fastening element being disposed adjacent the distal edge of the tape tab. More preferably, a portion of the adhesive securement means is disposed subjacent the first fastening element to join the first fastening element to the tape tab. Alternatively, the adhesive securement means may be disposed and exposed on more than one area of the tape tab so that the first fastening element is, for example, disposed between a first sub-area and a second sub-area of the adhesive securement means.

DETAILED DESCRIPTION OF THE INVENTION

Tape fastener systems of the present invention are useful and beneficial when applied to disposable absorbent articles. As used herein, the term "disposable absorbent article" refers to articles which absorb and contain body exudates and, more specifically, refers to articles which are placed against or in proximity to the body of the wearer to absorb and contain the various exudates discharged from the body and which are intended to be discarded after a single use (i.e., they are not intended to be laundered or otherwise restored or reused). A preferred embodiment of the disposable absorbent article of the present invention is a diaper 20. As used herein, the term "diaper" refers to a garment generally worn by infants or incontinent persons that is drawn up between the legs and fastened about the waist of the wearer. Examples of the kinds of diapers to which the present invention is very readily adapted are shown in the above-referenced U.S. Pat. Re. 26,151 issued to Duncan et al. and in U.S. Pat. No. 3,860,003 entitled "Contractable Side Portions for Disposable Diaper" which issued to Kenneth B. Buell on Jan. 14, 1975, both of which are incorporated herein by reference. It will be apparent from the following description that the tape fastener system illustrated and described herein may be applied to the body portion of such diapers. On the other hand, it will be understood that the invention is not limited to any specific diaper structure or configuration.

Figure 1:
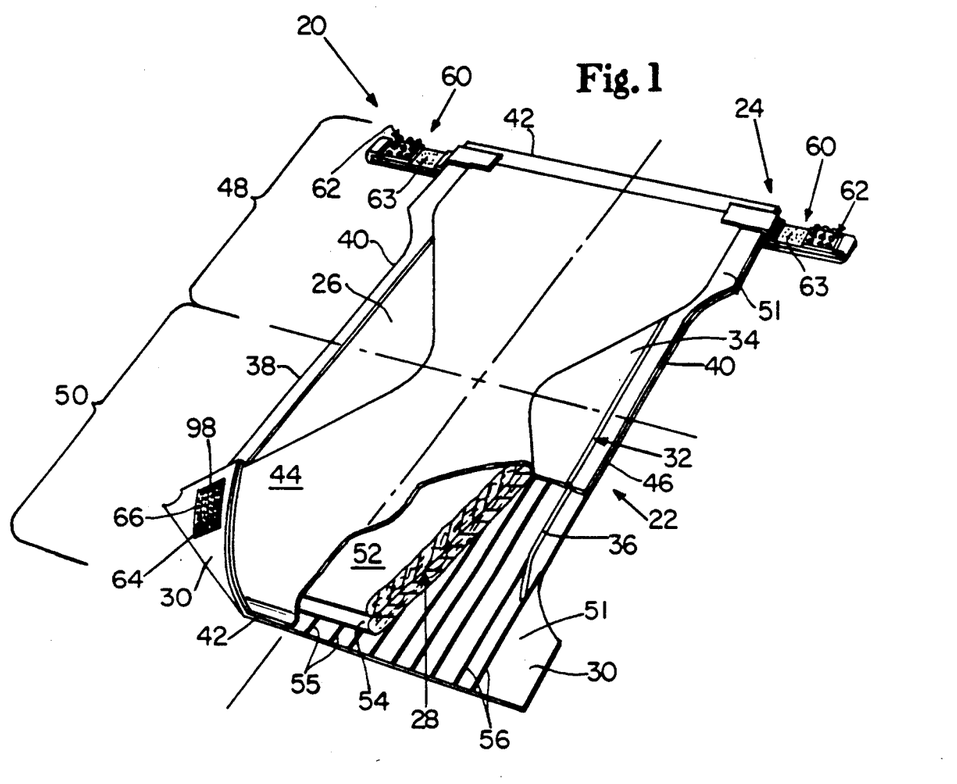
FIG. 1 is a partially cut-away perspective view of a diaper embodiment incorporating the present invention.

Referring to the drawings, it will be noted that FIG. 1 is a partially cut-away perspective view of the diaper 20 of the present invention prior to its being placed on the diaper wearer by the diaper user. As can be seen in FIG. 1, a preferred diaper 20 comprises a body portion 22 and a tape fastener system 24. A preferred body portion 22 comprises a liquid pervious topsheet 26, an absorbent core 28, a liquid impervious backsheet 30, and elastically contractible leg cuffs 32 comprising a side flap 34 and one or more elastic members 36. While the topsheet 26, the absorbent core 28, the backsheet 30, the side flaps 34, and the elastic members 36 may be assembled in a variety of well known configurations, a preferred disposable diaper configuration is shown and described generally in the above-referenced U.S. Pat. No. 3,860,003 which issued to Kenneth B. Buell on Jan. 14, 1975, and which patent is incorporated herein by reference.

FIG. 1 shows a preferred embodiment of the body portion 22 in which the topsheet 26 and the backsheet 30 are coextensive and have length and width dimensions generally larger than those of the absorbent core 28. The topsheet 26 is superposed on the backsheet 30 thereby forming the periphery 38 of the body portion 22. The periphery 38 defines the outer perimeter or, in other words, the outer extent of the body portion 22. The periphery 38 comprises longitudinal edges 40 and end edges 42.

The body portion 22 has an inside surface 44 and an outside surface 46. In general, the outside surface 46 of the diaper 20 extends from one end edge 42 to the other end edge 42 of the diaper and from one longitudinal edge 40 to the other longitudinal edge 40 of the diaper and is the surface farthest from the wearer during use of the diaper 20. When a backsheet 30 is used, it typically forms the outside surface 46 of the body portion 22. The inside surface 44 is that surface of the diaper opposite the outside surface 46 and in the embodiment shown is typically formed by the topsheet 26. In general, the inside surface 44 of the diaper 20 is that surface coextensive with the outside surface 46 and which is for the greater part in contact with the wearer when the diaper 20 is worn.

The diaper 20 has first and second end regions 48 and 50, respectively, extending from the end edges 42 of the diaper periphery 38 toward the lateral centerline of the diaper 20. Both the first end region 48 and the second end region 50 extend a distance of about one-half of the length of the diaper 20 such that the end regions comprise each half of the diaper 20.

Each of the first end regions 48 and the second end regions 50 have panels 51. The panels 51 are those portions of the first end region 48 and the second end region 50 which overlap when the diaper 20 is fastened about the waist of the wearer. The extent to which the end regions overlap and thus the extent to which the panels 51 are formed will depend on the overall dimensions and shape of the diaper 20 and the size of the wearer.

The absorbent core 28 of the body portion 22 may be any means which is generally compressible, conformable, non-irritating to the wearer's skin, and capable of absorbing and retaining liquids and certain body exudates. The absorbent core 28 may be manufactured in a wide variety of sizes and shapes (e.g., rectangular, hourglass, asymmetric, etc.) and from a wide variety of liquid absorbent materials commonly used in diapers and other disposable absorbent articles, such as comminuted wood pulp which is generally referred to as the airfelt. Examples of other suitable absorbent materials include creped cellulose wadding, absorbent foams, absorbent sponges, superabsorbent polymers, absorbent gelling materials, or any equivalent materials or combination of materials. The total absorbent capacity of the absorbent core 28 should, however, be compatible with the design exudate loading in the intended use of the diaper 20. Further, the size and absorbent capacity of the absorbent core 28 may be varied to accommodate wearers ranging from infants to adults.

While the absorbent core 28 may comprise a single layer of absorbent material such as the configuration described in U.S. Pat. No. 4,610,678 entitled "High-Density Absorbent Structure" which issued to Paul T. Weisman and Steven A. Goldman on Sept. 9, 1986 and which patent is incorporated herein by reference, a preferred embodiment of the absorbent core 28 is a dual-layered absorbent core in a preferred configuration such as is generally described in U.S. Pat. No. 4,673,402 entitled "Absorbent Article With Dual-Layered Cores" which issued to Paul T. Weisman, Dawn I. Houghton and Dale A. Gellert on June 16, 1987, and which is incorporated herein by reference, having an asymmetric-shaped upper layer 52 and a lower layer 54. The upper layer 52 preferably acts as a liquid acquisition/distribution layer comprised primarily of hydrophilic fiber material. The lower layer 54 acts as a fluid storage layer comprised of a mixture of hydrophilic fiber material and particles of an absorbent gelling material (hydrogel material). Each of the upper layer 52 and the lower layer 54 preferably comprises an absorbent layer encased in a tissue layer. It should be understood, however, that the size, shape, configuration, and total absorbent capacity of the upper layer 52 or the lower layer 54 may be varied to accommodate wearer's ranging from infants through adults. Therefore, the dimensions, shape, and configuration of both the upper layer 52 and the lower layer 54 may be varied (e.g., the upper layer or the lower layer may have a varying caliper, a hydrophilic gradient, a rapid acquisition zone or may contain absorbent gelling material).

The absorbent core 28 is superposed on the backsheet 30 and is preferably associated thereto by a core attachment means 55 such as those well known in the art, for example, pressure-sensitive adhesives, hot melt adhesives or other adhesives; ultrasonic bonding; or heat/pressure sealing. The absorbent core 28 may be secured to the backsheet 30 by a uniform continuous layer of adhesive, a patterned layer of adhesive, or any array of separate lines or spots of adhesive. An adhesive which has been found to be satisfactory is preferably a hot-melt adhesive such as manufactured by Eastman Chemical Products Company of Kingsport, Tennessee and marketed under the tradename of Eastobond A-3 or by Century Adhesives, Inc., of Columbus, Ohio and marketed under the tradename Century 5227. The core attachment means 55 preferably comprise an open pattern network of filaments of adhesive as is shown in U.S. Pat. No. 4,573,986 entitled "Disposable Waste-Containment Garment" which issued to James A. Minetola and David R. Tucker on Mar. 4, 1986, and which is incorporated herein by reference.

The backsheet 30 is impervious to liquids and is preferably manufactured from a thin plastic film, although other flexible liquid impervious materials may also be used. The backsheet 30 prevents the exudates absorbed and contained in the absorbent core 28 from soiling articles which contact the diaper 20 such as bedsheets and undergarments. Preferably, the backsheet 30 is a polyethylene film having a thickness of from about 0.012 mm (0.5 mil) to about 0.051 mm (2.0 mils), although other flexible, liquid impervious materials may be used. As used herein, the term "flexible" refers to materials which are compliant and which will readily conform to the general shape and contours of the human body.

A suitable polyethylene film is manufactured by Monsanto Chemical Corporation and marketed in the trade as Film No. 8020. The backsheet 30 is preferably embossed and/or matte finished to provide a more clothlike appearance. Further, the backsheet 30 may permit vapors to escape from the absorbent core 28 while still preventing exudates from passing through the backsheet 30.

The size of the backsheet 30 is dictated by the size of the absorbent core 28 and the exact diaper design selected. In a preferred embodiment, the backsheet 30 has a modified hourglass shape extending beyond the absorbent core a minimum distance of at least about 1.3 cm to about 2.5 cm (about 0.5 to 1.0 inch) around the entire diaper periphery 38.

The topsheet 26 of the body portion 22 of the present invention is compliant, soft feeling and non-irritating to the wearer's skin. Further, the topsheet 26 is liquid pervious permitting liquids to readily penetrate through its thickness. A suitable topsheet 26 may be manufactured from a wide range of materials such as porous foams, reticulated foams, apertured films, natural fibers (e.g., wood or cotton fibers), synthetic fibers (e.g., polyester or polypropylene fibers) or from a combination of natural and synthetic fibers. Preferably, it is made of a hydrophobic material to isolate the wearer's skin from liquids retained in the absorbent core 28.

A particularly preferred topsheet 26 comprises staple length polypropylene fibers having a denier of about 1.5, such as Hercules Type 151 polypropylene fibers marketed by Hercules, Inc. of Wilmington, Del. As used herein, the term "staple length fibers" refer to those fibers having a length of at least about 15.9 mm (0.625 inches).

There are a number of manufacturing techniques which may be used to manufacture the topsheet 26. For example, the topsheet 26 may be woven, non-woven, spunbonded, carded, hydroformed or the like. A preferred topsheet 26 is carded and thermally bonded by means well known to those skilled in the fabric art. Preferably, the topsheet 26 has a basis weight from about 15 to about 30 grams per square meter, a minimum dry tensile strength of at least about 400 grams per centimeter in the machine direction and a wet tensile strength of at least about 55 grams per centimeter in the cross-machine direction.

The topsheet 26 and the backsheet 30 are associated together in any suitable manner as is well known in the diaper manufacturing art. As used herein, the term "associated" encompasses configurations whereby the topsheet 26 is directly joined to the backsheet 30 by affixing the topsheet 26 directly to the backsheet 30, and configurations whereby the topsheet 26 is indirectly joined to the backsheet 30 by affixing the topsheet 26 to intermediate members which in turn are affixed to the backsheet 30. In a preferred embodiment, the topsheet 26 and the backsheet 30 are joined directly to each other in the diaper periphery 38 by a flap attachment means 56 such as an adhesive or any other attachment means as is known in the art. In general, the core attachment means 55 that affixes the absorbent core 28 to the backsheet 30 is the same means as the flap attachment means 56 that affixes the topsheet 26 to the backsheet 30. Thus, for example, a uniform continuous layer of adhesive, a patterned layer of adhesive, an array of separate lines or spots of adhesive, or a network of adhesive filaments such as shown in the above-referenced U.S. Pat. No. 4,573,986 may be used.

Elastically contractible leg cuffs 32 are disposed adjacent the periphery 38 of the body portion 22, preferably along each longitudinal edge 40 so that the leg cuffs 32 tend to draw and hold the diaper 20 against the legs of the wearer. While the leg cuffs 32 may comprise any of several means as are well known in the diaper art, a particularly preferred leg cuff construction comprises a side flap 34 and one or more elastic members 36, as is described in detail in the hereinbefore referenced U.S. Pat. No. 3,860,003. In addition, a method and apparatus suitable for manufacturing a disposable diaper having elastically contractible leg cuffs are described in U.S. Pat. No. 4,081,301 entitled "Method and Apparatus For Continuously Attaching Discrete, Stretched Elastic Strands to Predetermined Isolated Portions of Disposable Absorbent Articles" which issued to Kenneth B. Buell on Mar. 28, 1978, and which patent is incorporated herein by reference. In a preferred embodiment, the elastically contractible leg cuff 32 comprises a side flap 34 and an elastic member 36 comprising an elastic thread.

The diaper 20 is provided with a tape fastener system 24 for forming a side closure. Thus, the diaper 20 is fitted to the wearer and the first end region 48 and the second end region 50 are maintained in an overlapping configuration when the diaper 20 is worn.

In a preferred embodiment of the present invention as shown in FIG. 1, the tape fastener system 24 comprises a tape tab 60 disposed adjacent each longitudinal edge 40 of the body portion 22 in the first end region 48, each tape tab 60 comprising a first fastening element 62 joined to and disposed on a first area of the tape tab 60 and adhesive securement means 63 associated with and disposed on at least a second area of the tape tab 60 for securing at least the second area to another portion of the diaper 20 so that each tape tab has a combination mechanical and adhesive closure mechanism; and a landing member 64, preferably comprising both a second fastening element 66 engageable with the first fastening element 62 and a portion of the backsheet 30, disposed on the outside surface 46 of the body portion 22 in the second end region 50.

As shown in the drawings, the tape fastener system 24 preferably comprises a tape tab 60. Any of the well known configurations and constructions of a tape tab may be used. A preferred tap tab 60 is a Y-shaped tape tab as described in detail in U.S. Pat. No. 3,848,594 entitled "Tape Fastening System for Disposable Diaper" which issued to Kenneth B. Buell on Nov. 19, 1974, and which patent is incorporated herein by reference. Alternatively preferred tape tabs are described in detail in co-pending U.S. patent application Ser. No. 078,345 entitled "Disposable Diaper Having Wide Tapered Fastening Tapes" filed July 28, 1987 by Harold R. Burkhardt and Kenneth B. Buell, which is incorporated herein by reference. As shown in FIG. 1, a tape tab 60 is provided adjacent each longitudinal edge 40 of the body portion 22, most preferably in the first end region 48.

Figure 2:
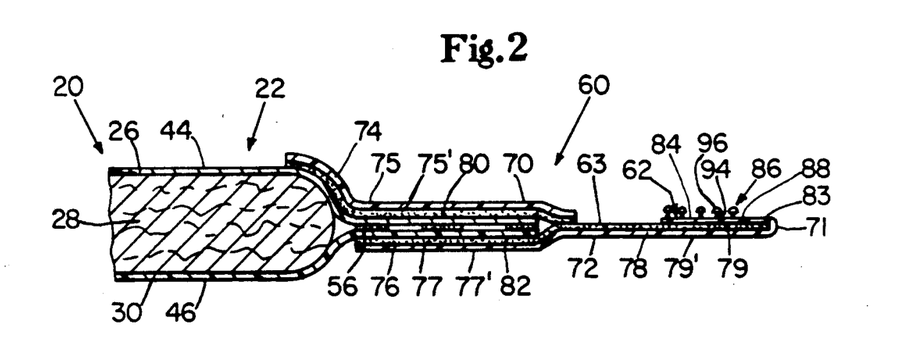
FIG. 2 is a cross-sectional view of the corner of the diaper taken along line 2—2 of FIG. 1.

A particularly preferred tape tab 60 is illustrated in FIG. 2 and has a fastening surface 70 and a backing surface 72. The fastening surface 70 is that surface of the tape tab 60 designed to engage the landing member 64 of the present invention. Thus, the fastening surface 70 of the tape tab 60 will generally correspond to the inside surface 44 of the body portion 22 and will have the adhesive securement means 63 and the first fastening element 62 disposed on it. The backing surface 72 is that surface opposite of the fastening surface 70 and generally corresponds to the outside surface 46 of the body portion 22. The backing surface 72 is thus generally exposed during wear of the diaper 20.

The preferred tape tab 60 illustrated in FIG. 2 is one which is anchored to both the inside surface 44 and the outside surface 46 of the body portion 22 to create a manufacturer's end (i.e., that attachment of the tape tab 60 to the diaper 20 made during manufacture of the diaper 20). The tape tab 60 has another element which forms the user's end (i.e., that joint made by the person in securing the diaper to the wearer). Thus, the preferred tape tab 60 of the present invention has at least three elements, a first fixed portion 74 having a first surface 75 and a second surface 75', a second fixed portion 76 having a first surface 77 and a second surface 77', and a connective portion 78 having a first surface 79 and a second surface 79'. The first fixed portion 74 is that portion of the tape tab 60 which is attached to the inside surface 44 of the body portion 22. The second fixed portion 76 is that portion of the tape tab 60 which is attached to the outside 46 of the body portion 22. The first fixed portion 74 and the second fixed portion 76 thus form the manufacturer's end of the tape tab 60. The connective portion 78 is that portion of the tape tab 60 which is attached to another portion of the diaper 20, generally the landing member 64, by the user when securing the diaper 20 on the wearer. The connective portion 78 thus forms the user's end. Additionally, the second surface 77' of the second fixed portion 76 and the second surface 79' of the connective portion 78 form the backing surface 72 of the tape tab 60 while the first surface 75 of the first fixed portion 74 and the first surface 79 of the connective portion 78 form the fastening surface 70 of the tape tab 60.

The preferred Y-shaped tape tab 60 of the present invention can be constructed in several ways. The first fixed portion 74, the second fixed portion 76, and the connective portion 78 can each be separate tapes which meet and are joined adjacent the longitudinal edge 40 of the body portion 22 in an area of joinder. A more practical structure for the tape tab 60 is one in which the connective portion 78 and either the first fixed portion 74 or the second fixed portion 76 is a unitary strip of tape material. If the connective portion 78 is unitary with the second fixed portion 76 as shown in FIG. 2, then the first fixed portion 74 is a separate element which is attached to the combined connective portion 78 and the second fixed portion 76 adjacent to the longitudinal edge 40 of the body portion 22 at an area of joinder 80.

FIG. 2 also shows tab attachment means for securing the tape tab 60 to the body portion 22. These tab attachment means are any of those attachment means which provide an adequate bond, and preferably are any of the pressure-sensitive adhesives well-known to those of ordinary skill in the adhesive art. The second surface 75' of the first portion 74 is affixed to the inside surface 44 of the body portion 22 by a first tab attachment means 80. The first surface 77 of the second fixed portion 76 is affixed to the outside surface 46 of the body portion 22 by a second tab attachment means 82. The connective portion 78 has an adhesive securement means 63 associated with it on the first surface 79. This adhesive securement means 63 forms a joint between the connective portion 78 and the landing member 64, preferably the backsheet 30, during use. Since the connective portion 78 and the second fixed portion 76 are preferably unitary as shown in FIG. 2, the adhesive securement means 63 and the second tab attachment means 82 are generally the same element coated onto the unitary structure in a continuous manner.

Preferred materials for the tape tabs 60 comprises a tape material such as tape code numbers XPF 14.43.0, Y-9376, or Y-9030 available from The Minnesota Mining and Manufacturing Company, St. Paul, Minn. The tape material in the embodiments are preferably a polyethylene film having a tab attachment means tailored to bond to the polyethylene positioned on the tape material. The tab attachment means may comprise any of those adhesives which provide an adequate bond with other portions of the diaper and is preferably any of the pressure-sensitive adhesives well known to those of ordinary skill in the art. Preferred tab attachment means is a pressure-sensitive adhesive such as code number XPF 1.42.34 available from The Minnesota Mining and manufacturing Company, St. Paul, Minn.

As shown in FIG. 2, the tape tab 60 may also have a grip tab 83 at the distal edge 71 of the connective portion 78. The grip tab may be formed by folding over a small margin of the distal edge 71 of the connective portion 78 and attaching it to itself. This forms an end on the connective portion 78 which is easier to grasp by the diaper user when the diaper 20 is to be fitted and attached to the wearer. The grip tab 83 is most beneficial when used when the connective portion 78 is superposed on the first fixed portion 74.

The first fastening element 62 of the tape tab 60 forms a closure between the tape tab 60 and the landing member 64. Thus, the first fastening element 62 provides an element or elements that engage the second fastening element 66 of the landing member 64 to provide a secure side closure. The first fastening element 62 may thus comprise any of the well known means for achieving a side closure such as hook fastening materials or loop fastening materials.

The first fastening element 62 may be a separate member joined to the tape tab 60 or a unitary member with the tape tab 60. For example, the tape tab 60 may be manufactured to have engaging elements formed or molded thereon so as to mechanically engage the landing member 64 (the tape tab 60 having a unitary first fastening element 62), or a discrete patch or strip of material may be joined to the tape tap 60 (a separate first fastening element 62). Preferably, the first fastening element 62 is a separate patch of material joined to a portion of the fastening surface 70 of the tape tab 60.

The first fastening element 62 is preferably joined to a portion of the fastening surface 70 of the tape tab 60. As used herein, the term "joined" encompasses configurations whereby the first fastening element 62 is releasably secured to the tape tab 60 so that the first fastening element 62 may be peeled away from the adhesive securement means 63 by the user especially after the diaper 20 has been soiled and whereby the first fastening element 62 is affixed to the tape tab 60 such that the first fastening element 62 is securely fastened to the tape tab 60. Joined is also used to denote that the first fastening element 62 may be directly joined to the tape tab 60 or may be indirectly joined to the tape tab 60 such as by releasably securing or affixing the first fastening element 62 to an intermediate member which in turn is releasably secured or affixed to the tape tab 60. Preferably, as shown in FIG. 2, the first fastening element 62 is directly affixed to the fastening portion 78 of the tape tab 60 by the adhesive securement means 63, although any other adhesive attachment means as is known in the art may be used to join the first fastening element 62 to the tape tab; for example, the adhesive attachment means may be placed on the first fastening element 62 separately and the combined material joined to the connective portion 78.

While the first fastening element 62 may be disposed anywhere on the fastening surface 70 of the tape tab 60, the first fastening element 62 is preferably disposed entirely on the connective portion 78 (user's end) of the tape tab 60. Additionally, while the first fastening element 62 may be disposed anywhere on the connective portion 78 such as adjacent the area of joinder 80 or in the middle section of the connective portion 78, the first fastening element 62 is preferably disposed adjacent the distal edge 71 so that the first fastening element 62 provides maximum fit adjustment of the diaper 20 on the wearer.

Figure 3:
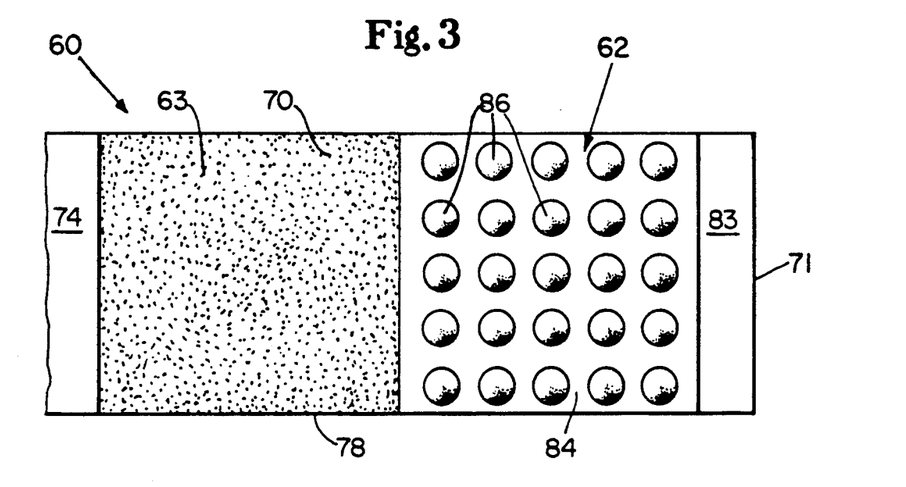
FIG. 3 is a plan view of the corner of the diaper shown in FIG. 2.

As shown in the drawings, the first fastening element 62 is disposed on a first area of the fastening surface 70 of the tape tab 60. Thus, the surface area of the first fastening element 62 generally defines the first area. The first area can have any desired shape, for example, rectangular, square, circular, oval, triangular, or trapezoidal. In preferred embodiments of the present invention as shown in FIG. 3, the first area will be rectangular-shaped.

In order to provide a combination mechanical and adhesive fastener system, the first area must comprise less than the total surface area of the fastening surface 70. Thus, it has been found that the first area should comprise between about 5% and about 95% of the total surface area of the fastening surface 70 of the tape tab 60. More preferably, the first fastening element 72 is disposed entirely on the connective portion 78 (user's end) of the tape tab 60. Thus, the first area preferably comprises between about 10% and about 90%, more preferably between about 20% and about 70%, of the total surface area of the connective portion 78. In an exemplary embodiment, the first area comprises about 33% of the total surface area of the connective portion 78 such that the first area is about 25 mm (about 1.0 inch) by about 12.5 mm (about ½ inch) (about 312.5 mm²).

FIG. 2 shows a preferred first fastening element 62 of the present invention. The first fastening element 62 of the present invention preferably comprises a hook fastening material 84. As used herein, the term "hook fastening material" is used to designate a material having engaging elements 86. Thus, the hook fastening material 62 may also be referred to as a made fastener. It should also be understood that the use of the term "hook" should be non-limiting in the sense that the engaging elements 86 may comprise any shape as are known in the art so long as they are adapted to engage a complementary second fastening element 66. As shown, the hook fastening material 84 preferably comprises a base 88 having a first surface and a second surface and a plurality of engaging elements 86 extending from the first surface of the base 88. Each of the engaging elements 86 are shown to comprise a stem 94 supported at one end on the first surface of the base 88 and an enlarged head 96 positioned at the end of the stem 94 opposite of the base 88.

The preferred hook fastening material 84 of the present invention is intended to engage fibrous elements of a loop fastening material so as to provide a secure fastening device. Thus, the hook fastening material 84 may be manufactured from a wide range of materials. Suitable materials include nylon, polyester, polypropylene, or any combination of these materials.

A suitable hook fastening material 84 comprises a number of shaped engaging element 86 projecting from a woven backing such as the commercially available material designated "Scotchmate" brand No. FJ3402 available from Minnesota Mining and Manufacturing Company, St. Paul, Minn. Alternatively, the engaging elements may have any shape such as hooks, "T's" or any other shape as are well known in the art. A particularly preferred hook fastening material is described in my co-pending U.S. patent application Ser. No. 07/007,841 entitled "Disposable Diaper Having An Improved Fastening Device" filed Jan. 26, 1987, and which is incorporated herein by reference.

The adhesive securement means 63 provides a layer of adhesive for securing at least a second area of the tape tab 60 to other portions of the diaper 20. The adhesive securement means 63 may also provide an attachment means for attaching the connective portion 78 of the tape tab 60 to the first fixed portion 74 and the second fixed portion 76, a means for joining the first fastening element 62 to the tape tab 60, and/or a disposal means for securing the diaper 20 in a configuration for disposal so as to contain the contents of the soiled diaper and provide convenient disposal of the diaper 20. Thus, the adhesive securement means 63 are any of those adhesives which provide an adequate bond with other portions of the diaper, and preferably is any of the pressure-sensitive adhesives well-known to those of ordinary skill in the adhesive art. The adhesive securement means 63 most preferably comprises a pressure-sensitive adhesive such as code number XPF 1.42.34 available from The Minnesota Mining and Manufacturing Company, St. Paul, Minn.

While the adhesive securement means 63 may be disposed anywhere on the fastening surface 70 of the tape tab 60, the adhesive securement means 63 is preferably disposed entirely on the connective portion 78 (user's end) of the tape tab 60. Additionally, while the adhesive securement means 63 may be disposed anywhere on the first surface 79 of the connective portion 78 of the tape tab 60 such as adjacent the distal edge 71 or in the middle section of the connective portion 78, the adhesive attachment means 63 is preferably disposed adjacent the first fastening element 62 and, more preferably, on at least a second area of the fastening surface 70.

As shown in the drawings, the adhesive securement means 63 is disposed on at least a second area of the fastening surface 70 of the tape tab 60. The second area is defined by the total exposed area of adhesive disposed on the fastening surface 70 or the first surface 79 of the connective portion 78 of the tape tab 60. Thus, the second area generally defines the area of the fastening surface 70 or the first surface 79 of the connective portion 78 not having a first fastening element 62 positioned on it such that adhesive securement means 63 is capable of being adhered to other portions of the diaper 20 during use. The second area can thus comprise one or more areas of adhesive and can have any desired shape, for example, rectangular, square, circular, oval, triangular, trapezoidal or any combination of shapes. In a preferred embodiment of the present invention as shown in FIG. 3, the second area will be rectangular-shaped.

In order to provide a combination mechanical an adhesive fastener system, the second area must comprise less than the total surface area of the fastening surface 70. Thus, it has been found that the second area should comprise between about 95% and about 5% of the total surface area of the fastening surface 70 of the tape tab 60. More preferably, the adhesive securement means 63 is disposed entirely on the connective portion 78 (user's end) of the tape tab 60. Thus, the second area preferably comprises between about 90% and about 10%, more preferably between about 80% and about 30%, of the total surface area of the first surface 79 of the connective portion 78. In an exemplary embodiment, the second area comprises about 67% of the total surface area of the first surface 79 of the connective portion 78.

While the first area and the second area are generally contiguous and together comprise about 100% of the total surface area available on the fastening surface 70 or the first surface 79 of the connective portion 78, the first area and the second area do not necessarily have to comprise 100% of the total surface area. For example, portions of the fastening surface 70 or the first surface 79 of the connective portion 78 may have neither an adhesive securement means 63 nor a first fastening element 62 disposed on it. This portion of the tape tab 60 may have nothing, some other fastening means, or release means disposed on it. Generally, however, the first area and the second area comprise about 100% of the total surface area of the first surface 79 of the connective portion 78 of the tape tab 60 so that the fastening surface 70 of the user's end consists of the adhesive securement means 63 and the first fastening element 62.

The adhesive securement means 63 is disposed on at least a second area of the fastening surface 70. Thus, the adhesive securement means 63 may be disposed on other areas of the fastening surface 70 of the tape tab 60. For example, the adhesive securement means 63 may be disposed adjacent the area of joinder 80 of the tape tab 60, the adhesive securement means 63 being covered by the first fixed portion 74. Additionally, the adhesive securement means 63 may be positioned subjacent the first fastening element 62 to join the first fastening element 62 to the tape tab 60, the adhesive securement means 63 being covered by the first fastening element 62. The adhesive securement means 63 may also be positioned adjacent the distal edge 71 of the tape tab 60 to form the grip tab 83. Thus, in preferred embodiments of the present invention, the adhesive securement means 63 is disposed in more than the second area of the tape tab 60, and is most preferably positioned on the entire first surface 79 of the connective portion 78 so as to act not only as a securement means but also as an attachment means for the first fixed portion 74, as a means for joining the first fastening element 62 to the tape tab 60, and as a means for creating the grip tab 83.

The adhesive securement means 63 may also provide a disposal means to allow the diaper 20 to be secured in a configuration for disposal so as to allow the diaper to be conveniently thrown away in a waste receptacle. For example, if the first fastening element 62 is affixed to the fastening surface 70, the exposed portion of the adhesive securement means 63 in the second area may be affixed to portions of the other tape tab 60 or to the body portion 22 of the diaper 20 such as the backsheet 30 so as to secure the diaper 20 in its disposal configuration. Alternatively, if the first fastening element 62 is releasably secured to the tape tab 60 by the adhesive securement means 63, after the diaper 20 has been soiled and configured for disposal, the first fastening element 62 is peeled away from the adhesive which is used to secure the diaper 20 in its disposal configuration by affixing the adhesive to the other tape tab 60 or to the body portion 22 of the diaper 20 such as the backsheet 30. Example of how a diaper may be configured for disposal and of disposal means are shown in A. J. Robertson's and my co-pending U.S. Patent Application entitled "Mechanical Fastening Systems With Disposal Means For Disposable Absorbent Articles", which is incorporated herein by reference.

The landing member 64 of the tape fastener system 24 provides a means for securing itself and the tape tab 60 together to maintain the first end region 48 and the second end region 50 in an overlapping configuration. The landing member 64 may be disposed anywhere on the diaper 20 so long as it engages the tape tab 60 so as to maintain a side closure. For example, the landing member 64 may be disposed on the outside surface 46 in the second end region 50, on the inside surface 44 in the first end region 48, or on any other portion of the diaper 20 which is disposed to engage the tap 60. In addition, the landing member 64 may be a discrete separate element affixed to the diaper 20, a unitary piece of material that is neither divided nor discontinuous with an element of the diaper 20 such as the topsheet 26 or the backsheet 30, or a combination of unitary and separate elements. While the landing member 64 can assume varying sizes and shapes, it preferably comprises a portion of the backsheet 30 and one or more separate patches of material positioned across the outside surface 46 of the body portion 22 in the second end region 50 to allow for maximum fit adjustment at the waist of the wearer. The preferred embodiment of the landing member 64 illustrated in FIG. 1 comprises an elongated, rectangular-shaped, second fastening element 66 secured to the outside surface 46 of the body portion 22 in the second end region 50 in the panels 51 adjacent each of the longitudinal edges 40 and a portion of the backsheet 30.

The landing member 64 preferably comprises a second fastening element 66 engageable with the first fastening element 62 of the tape tab 60. Thus, the second fastening element 66 may be manufactured from a wide range of materials and configurations capable of securely engaging the first fastening element 62. For example, the second fastening element 66 may comprise identical complementary elements with the first fastening element 62 or distinct complementary elements with the first fastening element 62. As used herein, the term "identical complementary element" is used to define mechanical fastening systems wherein the engaging elements of the first fastening element 62 and the second fastening element 66 comprise the same configuration or structure that are interlocking. Examples of such systems are described in U.S. Pat. Nos. 4,322,875 entitled "Two Strip Materials Used For Forming Fasteners" issued to Brown et al. on Apr. 16, 1982 and U.S. Pat. No. 4,701,179 entitled "Fixed Position Fasteners For Disposable Absorbent Garments" issued to Kellenberger et al. on Oct. 20, 1987. The term "distinct complementary elements" is used herein to designate a system wherein the first fastening element 62 is different from the second fastening element 66 but is engageable therewith such as buttons and holes, a hook fastening material and a loop fastening material, or a male member and a female member. Preferably, the second fastening element 66 comprises a hook fastening material or a loop fastening material depending upon whether the first fastening element 62 is a loop fastening material or a hook fastening material. As shown in FIG. 1, the landing member 64 preferably comprises a second fastening element 66 comprising a plurality of fiber elements such as a loop fastening material 98.

The loop fastening material 98 of the second fastening element 66 provides a plurality of fiber elements that engage the engaging elements 86 of the hook fastening material 84. The loop fastening material 98 may be manufactured from a wide range of materials to provide fiber elements, preferably loops. Such suitable materials include nylon, polyester, polypropylene, or any combination of these materials. A suitable loop fastening material 98 comprises a number of fiber loops projecting from a woven backing such as the commercially available material designated "Scotchmate" brand nylon woven loop No. SJ3401 available from Minnesota Mining and Manufacturing Company, St. Paul, Minn. A preferred loop fastening material 98 comprises a tricot knit fabric having a plurality of nylon filament loops projecting from a backing of nylon such as the commercially available material designated "Guilford No. 16110" available from Guilford Mills of Greensboro, N.C. Alternatively, the loop fastening material 98 may be a non-woven fabric or any other type of fiber material or loop material which are well known in the art. An inexpensive loop fastening material and a method of making such a loop fastening material is described in U.S. patent application Ser. No. 040,520, entitled "Loop Fastening Material For Fastening Device And Method Of Making Same" filed Apr. 24, 1987, by C. Locke Scripps and J. Richard Noel, which application is incorporated herein by reference.

In use, the diaper 20 is applied to the wearer by positioning the first end region 48 under the wearer's back and drawing the remainder of the diaper 20 between the legs of the wearer so that the second end region 50 is positioned across the front of the wearer. The fastening portion 78 of the tape tabs 60 are then secured to the landing members 64 positioned on the outside surface 46 of the second end region 50 so that the first fastening element 62 will engage the second fastening element 66 and the adhesive securement means 63 will adhere to the backsheet portion of the landing member 64 to form a side closure. After the diaper 20 has been soiled, the diaper 20 is removed from the wearer. The panels 51 in the second end region 50 may then be in-folded, and the body portion 22, beginning with the second end region 50, folded or rolled into a structure with the tape tabs 60 extending outwardly from the rolled-up diaper 20. The adhesive securement means 63 is then secured to either the other tape tab 60 or the body portion 22 such as the backsheet 30 so as to secure the diaper 20 in its rolled-up configuration so that it may be easily and conveniently disposed in a waste receptacle.

Figure 4:
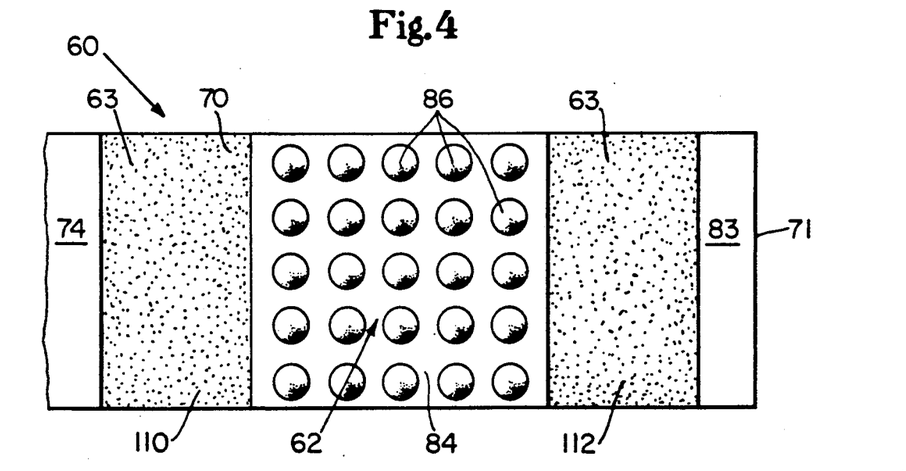
FIG. 4 is a plan view of the corner of an alternative embodiment of the diaper.

FIG. 4 shows an alternative embodiment of the present invention wherein the tape tab 60 comprises an adhesive securement means 63 disposed in a second area that comprises a first sub-area 110 and a second sub-area 112. The first sub-area 110 is disposed between the area of joinder 80 and the first fastening element 62 and the second sub-area 112 is disposed adjacent the distal edge 71 of the tape 60, between the first fastening element 62 and the grip tab 83. Thus, the first fastening element 62 is disposed between the first sub-area 110 and the second sub-area 112 of the adhesive securement means 63.

While particular embodiments of the present invention have been illustrated and described, it would be obvious to those skilled in the art that various other changes and modifications can be made without departing from the spirit and scope of the invention. It is therefore intended to cover in the appended claims all such changes and modification that are within the scope of this invention.

What is claimed is:

1. A disposable absorbent article comprising:
   a body portion having an inside surface, an outside surface opposite of said inside surface, longitudinal edges, a first end region, and a second end region opposite of said first end region, and comprising a liquid pervious topsheet, a liquid impervious backsheet joined to said topsheet, and an absorbent core disposed between said topsheet and said backsheet; and
   a tape fastener system positioned on said body portion and comprising
   (a) a tape tab disposed adjacent each longitudinal edge in said first end region, each of said tape tabs comprising (i) a fixed portion attached to said body portion,
(ii) a connective portion joined to said fixed portion adjacent said longitudinal edge, said connective portion having a fastening surface, a backing surface opposite of said fastening surface, and a distal edge spaced from said longitudinal edge of said body portion,
(iii) a first mechanical fastening means for mechanically engaging complementary elements to form a closure for the absorbent article, said first mechanical fastening means comprising a first fastening element joined to and disposed on a first area of said fastening surface, said first fastening element having elements capable of mechanically engaging complementary elements, and
(iv) adhesive securement means associated with and disposed on at least a second area of said fastening surface of said connective portion of said tape tab for adhesively securing at least said second area of said tape tab to another portion of the absorbent article to at least form a closure for the absorbent article so that each of said tape tabs has a combination mechanical and adhesive closure mechanism; and
(b) at least one landing member disposed on said outside surface in said second end region, said landing member comprising a second mechanical fastening means for mechanically engaging complementary elements to form a closure with said first mechanical fastening means for the absorbent article, said second mechanical fastening means comprising a second fastening element having elements mechanically engageable with said elements of said first fastening element.

2. The absorbent article of claim 1 wherein said first fastening element is a separate element joined to said tape tab.

3. The absorbent article of claim 2 wherein said adhesive securement means is additionally disposed subjacent said first fastening element in said first area of said fastening surface.

4. The absorbent article of claim 3 wherein said first fastening element is releasably secured to said tape tab by said adhesive securement means.

5. The absorbent article of claim 3 wherein said first fastening element is affixed to said tape tab by said adhesive securement means.

6. The absorbent article of claim 4 or 5 wherein said first fastening element is disposed adjacent said distal edge of said tape tab.

7. The absorbent article of claim 1 wherein both said adhesive securement means and said first fastening element are disposed entirely on said connective portion of said tape tab.

8. The absorbent article of claim 7 wherein said first fastening element is a separate element joined to said tape tab.

9. The absorbent article of claim 8 wherein said first fastening element is disposed adjacent said distal edge.

10. The absorbent article of claim 7 wherein a portion of said adhesive securement means is additionally disposed subjacent said first fastening element in said first area of said fastening surface.

11. The absorbent article of claim 10 wherein said first fastening element is a separate element joined to said tape tab.

12. The absorbent article of claim 11 wherein said first fastening element is releasably secured to said tape tab by said adhesive securement means.

13. The absorbent article of claim 12 wherein said first fastening element is positioned adjacent said distal edge.

14. The absorbent article of claim 13 wherein said first fastening element and said second fastening element are identical complementary elements.

15. The absorbent article of claim 13 wherein said first fastening element and said second fastening element are distinct complementary elements.

16. The absorbent article of claim 15 wherein said first fastening element comprises a hook fastening material and said second fastening material comprises a loop fastening material.

17. The absorbent article of claim 11 wherein said first fastening element is affixed to said tape tab by said adhesive securement means.

18. The absorbent article of claim 17 wherein said first fastening element is positioned adjacent said distal edge.

19. The absorbent article of claim 18 wherein said first fastening element and said second fastening element are identical complementary elements.

20. The absorbent article of claim 18 wherein said first fastening element and said second fastening element are distinct complementary elements.

21. The absorbent article of claim 20 wherein said first fastening element comprises a hook fastening material and said second fastening material comprises a loop fastening material.

22. The absorbent article of claim 1 wherein said adhesive securement means is disposed in at least a second area that comprises a first sub-area and a second sub-area, said first fastening element being disposed in a first area, said first area being disposed between said first sub-area and said second sub-area.

23. A disposable absorbent article comprising:
a body portion having an inside surface, an outside surface opposite of said inside surface, longitudinal edges, a first end region, a second end region opposite of said first end region, and comprising a liquid pervious topsheet, a liquid impervious backsheet joined to said topsheet, and an absorbent core positioned between said topsheet and said backsheet; and
a tape fastener system positioned on said body portion and comprising
(a) a tape tab disposed adjacent each longitudinal edge in said first end region, each of said tape tabs comprising
a first fixed portion having a first surface and a second surface opposed to said first surface,
first tab attachment means associated with said first fixed portion and said inside surface of said body portion for attaching said second surface of said first fixed portion to said inside surface,
a second fixed portion having a first surface, and a second surface opposed to said first surface,
second tab attachment means associated with said second fixed portion and said outside surface of said body portion for attaching said first surface of said second fixed portion to said outside surface,
a connective portion joined to said first fixed portion and said second fixed portion in an area of joinder adjacent said longitudinal edge of said body portion, said connective portion having a distal edge spaced from said area of joinder, a first surface, and a second surface opposite of said first surface, a first mechanical fastening means for mechanically engaging complementary elements to form a closure for the absorbent article, said first mechanical fastening means comprising a hook fastening material joined to and disposed on at least a first area of said first surface of said connective portion, said hook fastening material having engaging elements capable of mechanically engaging complementary elements, and adhesive securement means associated with and disposed on at least a second area of said first surface of said connective portion for adhesively securing at least said second area to another portion of the absorbent article to at least form a closure for the absorbent article so that each of said tape tabs has a combination mechanical and adhesive closure mechanism, said adhesive securement means comprising a layer of adhesive; and (b) at least one landing member disposed on said outside surface in said second end region, said landing member comprising a second mechanical fastening means for mechanically engaging complementary elements to form a closure with said first mechanical fastening means for the absorbent article, said second mechanical fastening means comprising a loop fastening material having a plurality of fiber elements mechanically engageable with said engaging elements of said hook fastening material disposed on said tape tabs.

24. The absorbent article of claim 23 wherein said hook fastening material is a separate element joined to said tape tab.

25. The absorbent article of claim 24 wherein a portion of said adhesive securement means is additionally disposed subjacent said hook fastening material on said first area of said fastening surface.

26. The absorbent article of claim 25 wherein said hook fastening material is positioned adjacent said distal edge.

27. The absorbent article of claim 26 wherein said second fixed portion and said connective portion are unitary.

28. The absorbent article of claims 25, 26, or 27 wherein said hook fastening material is releasably secured to said tape tab by said adhesive securement means.

29. The absorbent article of claims 25, 26 or 27 wherein said hook fastening material is affixed to said tape tab by said adhesive securement means.

30. The absorbent article of claims 23, 25 or 27 wherein said first area comprises between about 10% and about 90% of the total surface area of said first surface of said connective portion.

31. The absorbent article of claim 27 wherein said tape tab additionally comprises a grip tab.

* * * * *